United States Patent [19]

Tawil

[11] Patent Number: 5,225,976
[45] Date of Patent: Jul. 6, 1993

[54] AUTOMATED HEALTH BENEFIT PROCESSING SYSTEM

[75] Inventor: Jack J. Tawil, Richland, Wash.

[73] Assignee: Research Enterprises, Inc., Richland, Wash.

[21] Appl. No.: 668,035

[22] Filed: Mar. 12, 1991

[51] Int. Cl.[5] .................. G06F 15/22; G06F 15/24; G06G 7/52
[52] U.S. Cl. .................................. 364/401; 364/406
[58] Field of Search .............................. 364/401, 406

[56] References Cited

U.S. PATENT DOCUMENTS 4,858,121  8/1989  Barber et al. ................. 364/406

*Primary Examiner*—Roy Envall
*Assistant Examiner*—Ari M. Bai
*Attorney, Agent, or Firm*—Hopgood, Calimafde, Kalil, Blaustein & Judlowe

[57] ABSTRACT

An automated health benefit processing system. The system includes a database and three processors. The database includes, for each geographic area and for each medical procedures for which a benefit is payable, the benefit payable to an insured if the procedure is prescribed and performed, a list of providers available to perform the designated procedure, and each provider's charge for performing the designated procedure. The first processor generates a treatment plan concerning the insured that specifies the identity of the insured and the medical procedures to be performed on the insured. The first processor also accesses the database to retrieve the information stored in the database under the medical procedures to be performed and to append this information to the treatment plan. The second processor generates a treatment record specifying the medical procedures actually performed by a provider and the provider's actual charge therefor. The third processor processes the information in the treatment plan and treatment records to determine amounts payable to the insured and the provider.

17 Claims, 7 Drawing Sheets

AUTOMATED HEALTH BENEFIT PROCESSING SYSTEM

BACKGROUND OF THE INVENTION

This invention relates to a health benefit processing system. More specifically, it relates to an automated health benefit processing system which provides cost savings.

In recent years costs associated with health care have been rapidly increasing. A variety of systems which utilize specially designed computer hardware have been developed in an effort to ease the burden of processing claims relating to health benefits and to try to contain the rising costs.

An article in the Jan. 9, 1991 edition of the Wall Street Journal at page B1 discusses several of these systems. According to the article, a system provided by GMIS Clinical Information Service uses a database of health procedures and costs to evaluate claims. Another system, provided by Health Information Technologies, provides an electronic network linking physicians to insurers to eliminate paper claim forms. Yet another system allows hospitals and insurers to monitor the quality of health care delivery and is provided by MediQual.

None of these systems, however, provide an automated benefit processing system which reduces health care costs by quickly informing purchasers of medical services of market conditions such as the identity of providers of the services, their qualifications and their prices. Such a system, therefore, is needed to help contain increasing health care costs.

SUMMARY OF THE INVENTION

The present invention is an automated health benefit processing system which includes a database and processing means for performing processing of health benefit claims that result when an insured seeks medical services.

The database lists, for each geographic area and for each medical procedure which can be performed, the following information: the benefit payable if the designated medical procedure is prescribed and performed, a list of providers available to perform the designated procedure and each provider's charge for performing the designated procedure. It is preferable to also include background information concerning each provider. Further, the database can also be organized to provide this information based on a group of medical procedures which are related to a particular illness or injury.

A first processor generates a treatment plan concerning the insured which specifies the identity of the insured and one or more medical procedures to be performed. The first processor also accesses the database to append the information therein associated with the medical procedures to be performed to the treatment plan.

A second processor generates a treatment record concerning the insured which specifies the medical procedures actually performed by a provider as well as the provider's charge for performing the medical procedures. A third processor is provided to process the treatment plan and the treatment record to determine amounts payable to the insured and to the provider based on the benefit payable for the procedures actually performed and on the actual charges.

It is an object of the present invention to provide a health benefit processing system that is automated.

It is a further object of the present invention to provide a health benefit processing system that quickly and efficiently informs patients of market conditions.

DESCRIPTION OF THE PREFERRED EMBODIMENT

The following is a list of terms utilized throughout this specification:

Insurer: The entity which insures a number of parties and which processes or has processed claims of the insured parties.

Insured: A party which is insured by the insurer, including the person and his or her dependents covered by a policy issued by the insurer.

Patient: A person receiving health services.

Provider: Any person or entity providing medical treatment procedures or health related services.

Physician: A doctor who conducts an initial or diagnostic examination of an insured to determine what medical services are needed.

Figure 1:
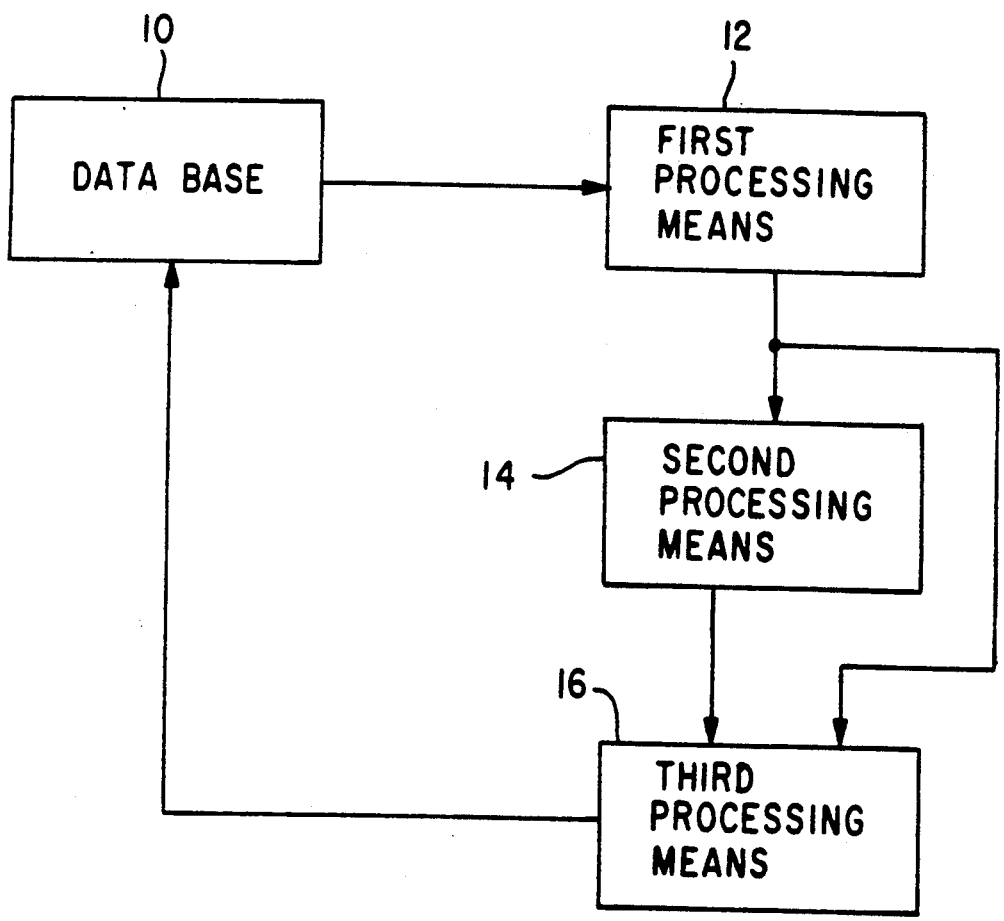
FIG. 1 illustrates a block diagram of an automated health benefit processing system in accordance with the present invention.

FIG. 1 illustrates a block diagram of an automated health benefit processing system, in accordance with the present invention with which an insurer processes the claims of its insured. The claims result when an insured—including the insured person and any dependents covered by the policy—seeks medical services. The system includes a database 10, a first processing means 12, a second processing means 14 and a third processing means 16.

The database 10 preferably specifies information for each relevant geographic area and for each medical procedure. This information includes a fixed benefit or payment payable to an insured if the procedure is prescribed and performed, a list of medical service providers able to perform the procedure and the price charged by each provider for that medical procedure.

The listed price in the database 10 can be a price recently charged by the provider. For example, the listed price can be the price charged by a provider on the most recent insurance claim. In this example, the listed price in the database 10 is updated each time a claim is processed by the system of FIG. 1. If such frequent updating creates system difficulties, the database 10 can alternatively be updated at a regular interval, for example, once a week. In a preferred embodiment, however, the listed price in the database 10 is a guaranteed price that is agreed to by the provider.

The applicable geographic area is the area wherein a patient can conveniently travel to obtain the service. The providers listed in the database 10 include physicians, dentists, hospitals, optometrists, pharmacies, testing laboratories and any other entity at which a patient can incur expenses that are covered under the insured's policy.

It is further preferred to include background information concerning each provider in the database 10. For example, for each provider, it is preferred to include medical specialties and board certification, number of years in practice, medical degrees with class rank, residency location, the number of malpractice suits lost and settled, any hospital affiliations, any university affiliations as well as any credit cards by which payment can be made. Also, the number of times the provider has performed the procedure within a given amount of time, for example, one year, can be provided. Since this last information is analyzed by the third processing means 16 when claims are processed, the number of times the procedure has been performed can be updated every time a claim is processed or periodically on a less frequent basis.

The database 10 can be sorted by individual medical procedures, in which case, every provider of each medical procedure and related information is listed. In this case, it is preferred to refer to each medical procedure by a coded number which is generally referred to by the medical industry as a Current Procedural Terminology (CPT) code.

The database 10 can also specify medical diagnostic descriptions associated with a particular episode of illness or injury. In this case, it is preferred to refer to each medical diagnosis by means of a coded number that the medical industry, particularly Medicare, typically refers to a Diagnostic-Related Group (DRG) code. When information is classified under DRG codes in the database 10, it is preferred to indicate providers capable of performing, or assuming responsibility for, the full range of procedures for treating the indicated episode of illness or injury, to the extent possible. Preferably, the database 10 includes the information stored under both sets of codes so that claims can be processed when CPT or DRG or both codes are specified. The database 10 also preferably includes, for each CPT and DRG code, a description thereof.

When medical services are required by an insured patient, a physician conducts a diagnostic examination of the insured patient. The physician determines the medical services and pharmaceutical prescriptions which are needed to treat the insured through the examination.

Figure 2:
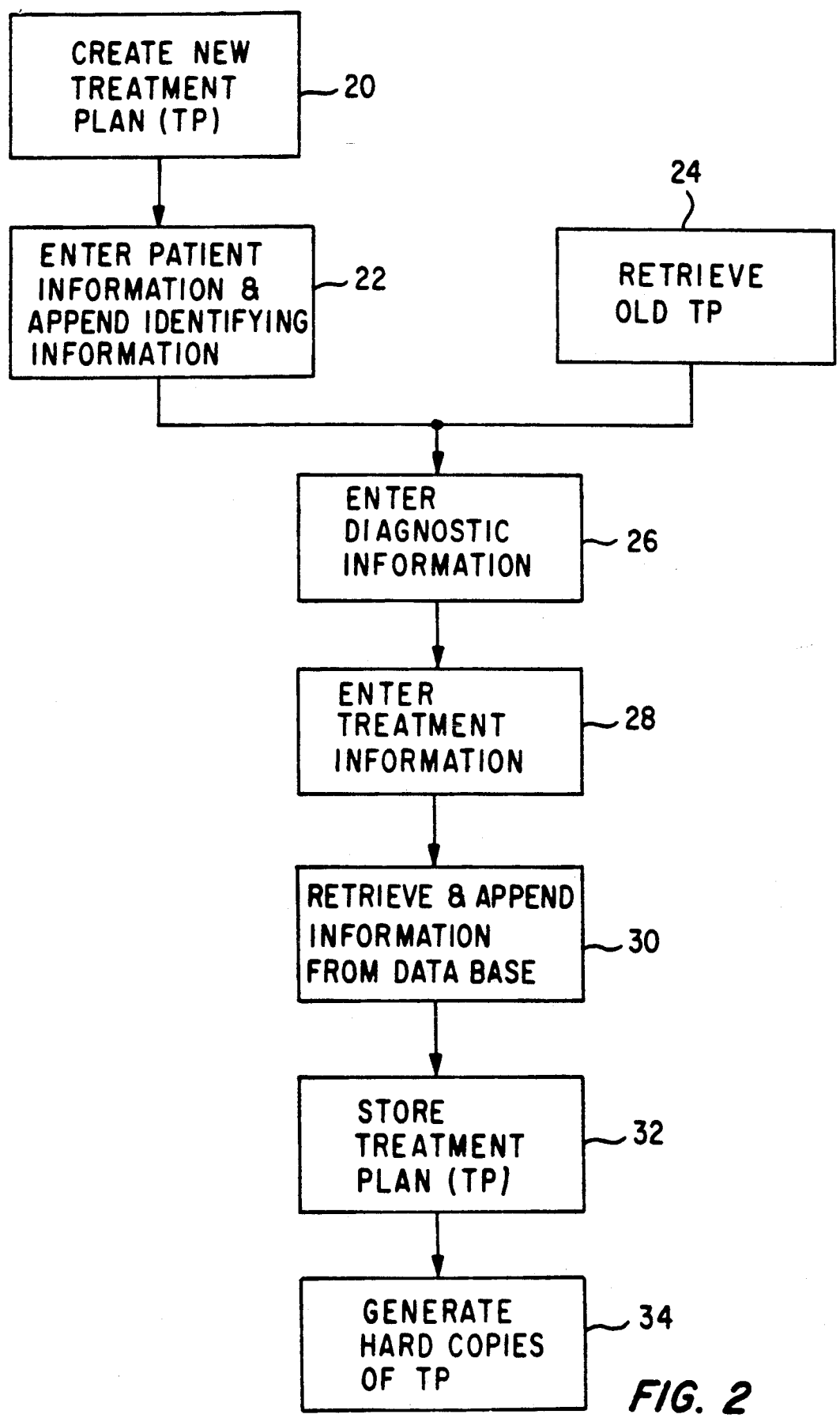
FIG. 2 illustrates a preferred procedure used by the automated health benefit processing system of FIG. 1 to generate a treatment plan.

After the examination, if necessary, the physician generates a treatment plan for the insured patient on the first processing means 12 in accordance with a preferred procedure as illustrated in FIG. 2. If this is the insured patient's first examination for a particular illness or injury, then a new treatment plan is created in step 20 and information concerning the patient is entered into the treatment plan in step 22. This information preferably includes the patient's and the insured's name, address, phone number, and social security number. The first processing means 12, in step 22, also automatically appends additional identifying information to the treatment plan. Preferably, the physician's identification number and the examination date are added and a number is assigned to the treatment plan. Also appended are the insurer's name and the status of the treatment plan (i.e., new or continuing).

If the patient is consulting the physician concerning an illness or injury for which a treatment plan has already been generated, however, that treatment plan is retrieved in step 24. Since the patient information and the identifying information have already been added to this treatment plan, step 22 need not be repeated.

In step 26, CPT codes associated with any diagnostic information or comments are entered. For example, any laboratory test results are included here. Also, observed symptoms can be included in the treatment plan during this step. Next, in step 28, information concerning the treatment recommended as a result of the diagnostic examination is entered into the treatment plan. A DRG code number designating the episode of the illness or injury requiring treatment (i.e. the diagnosis) is preferably entered. CPT code numbers designating the medical diagnostic procedures to be performed are also preferably entered into the first processing means 12. Also, any pharmaceutical prescriptions are entered. Finally, the recommended frequency of treatment (e.g., two times a week) and the recommended duration of each treatment (e.g., one month) are entered into the first processing means 12.

In step 30, the first processing means 12 accesses the database 10 using the CPT codes and the DRG code previously entered in the treatment plan in step 26 to retrieve the information stored in the database 10. Note that CPT codes or DRG codes can be used alone, however, it is preferred to use both. The retrieved information includes a list of providers able to perform the services specified by the CPT codes and the DRG code and their prices for doing so. Background information concerning each provider, if available, is also retrieved. It is further preferred that the information in the database 10 be accessed based on the geographic location convenient to the insured's residence. The information retrieved from the database 10 is appended to the treatment plan.

The first processing means 12, in step 32, stores the treatment plan as generated in steps 26, 28 and 30. It is preferred to store the generated treatment plan with all other treatment plans generated that day in a directory for later transfer to the third processing means 16. The treatment plan is also preferably stored on separate magnetic mediums, such as floppy disks, for the physician and for the patient.

Next, the first processing means 12 produces hard copies of the treatment plan in step 34. The hard copies are preferably distributed as follows: Two copies are distributed to the patient, a first to be given to a medical services provider to refer to and a second for the insured's records; a third copy is transmitted directly to the insurer; and a fourth copy is retained by the physician for his records. These copies are merely intended for informational purposes and are not needed by the system to process claims unless the provider lacks the capability to receive treatment plans electronically from the examining physicians, in which case the hard copy or the floppy disk of the treatment plan can be provided by the patient.

The treatment plan and the appended provider information, therefore, are available for review by the patient to assist the patient's decision making process. For example, the patient can determine the benefit payable for the medical procedures to be performed. The patient can also determine the price each provider will charge for performing the procedures if the price is a guarantee or, if the price is the latest one charged by the provider, the patient can determine the latest market prices for the procedure and make a selection accordingly. Additionally, if background information is available concerning the providers, then the patient can make a more informed selection as to the likely quality of the services to be provided.

The first processing means 12 can also include a diagnostic software package as well as a diagnostic database to assist in the diagnostic examination. The software package can be any of the available artificial intelligence medical diagnoses systems. The diagnostic database would preferably associate sets of symptoms to specific diagnoses. These associations would be a statistically base system that would be updated by the third processing means 16 as claims are processed. For example, the set of symptoms and the associated diagnosis can be determined from the treatment plans. The appropriateness of the diagnosis can be determined from later treatment and can be included in the diagnostic database. Such a database would be generated by the third processing means 16 from information derived from the treatment plans and the later treatment during claims processing.

When the patient seeks a provider to perform the medical procedures listed in the treatment plan, the patient can instruct the office of the physician where the treatment plan was generated to have the first processing means 12 electronically send the treatment plan to the second processing means 14 which will be used by the selected provider to further process the patient's claim. Alternatively, a magnetic medium or hard copy of the treatment plan can be given to the provider by the patient.

The second processing means 14 can either be in the provider's office or can be a centrally located processor to which all providers have access through data entry means in the providers' office. In the case of a centrally located second processing means 14, the first processing means 12 can automatically transmit the treatment plan to the second processing means 14 once the plan is complete. Then, regardless of which provider is sought, the information will be accessible. Further in the case of centrally provided second processing means 14, to reduce the potential for fraud, it is preferred that the provider's access to treatment plans be limited to the treatment plan for the patient being treated. This can be accomplished by providing access codes for each treatment plan which the provider learns from the patient or from the insurer.

Figure 3:
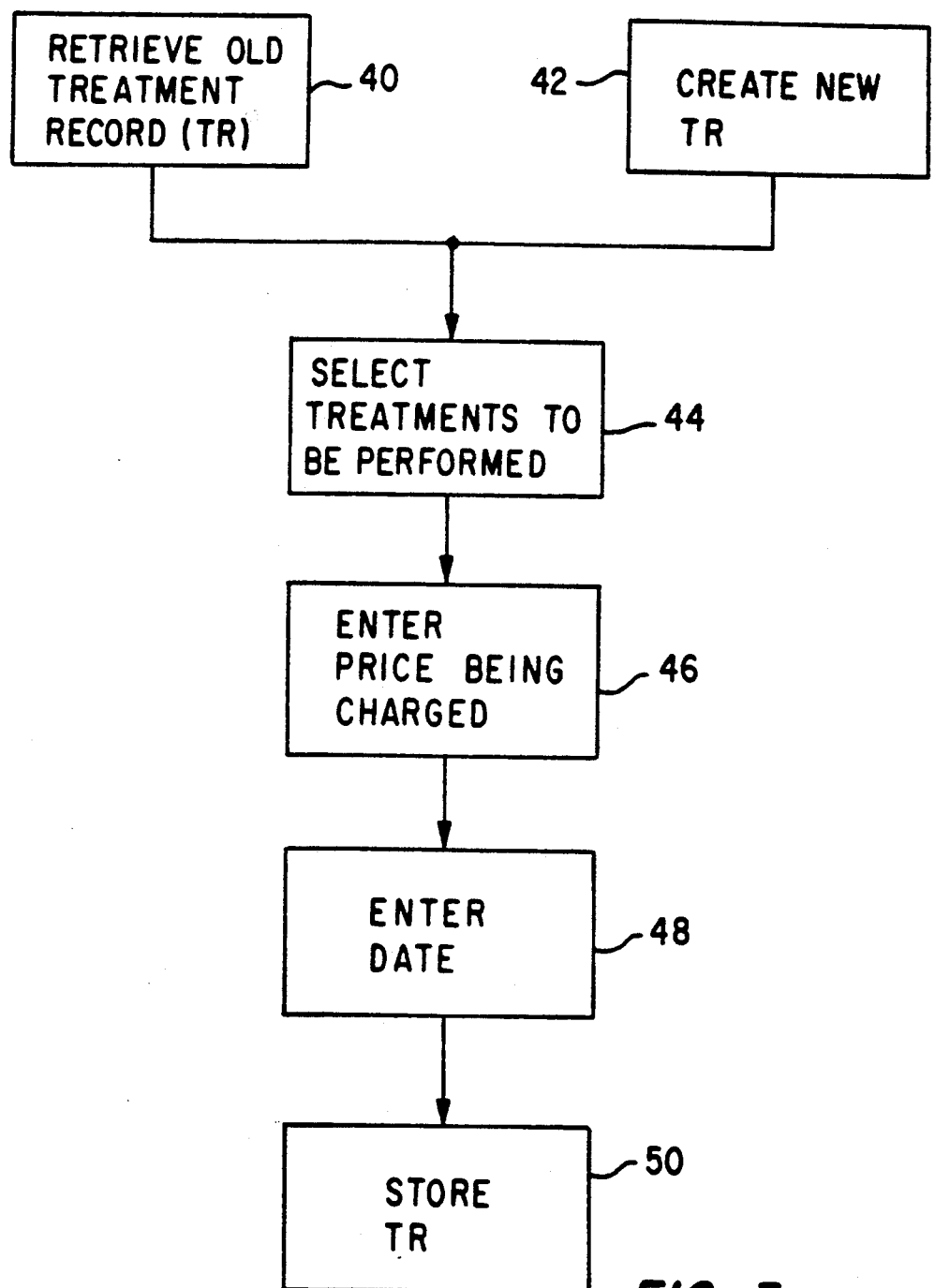
FIG. 3 illustrates a preferred procedure used by the automated health benefit processing system of FIG. 1 to generate a treatment record.
Figure 4:
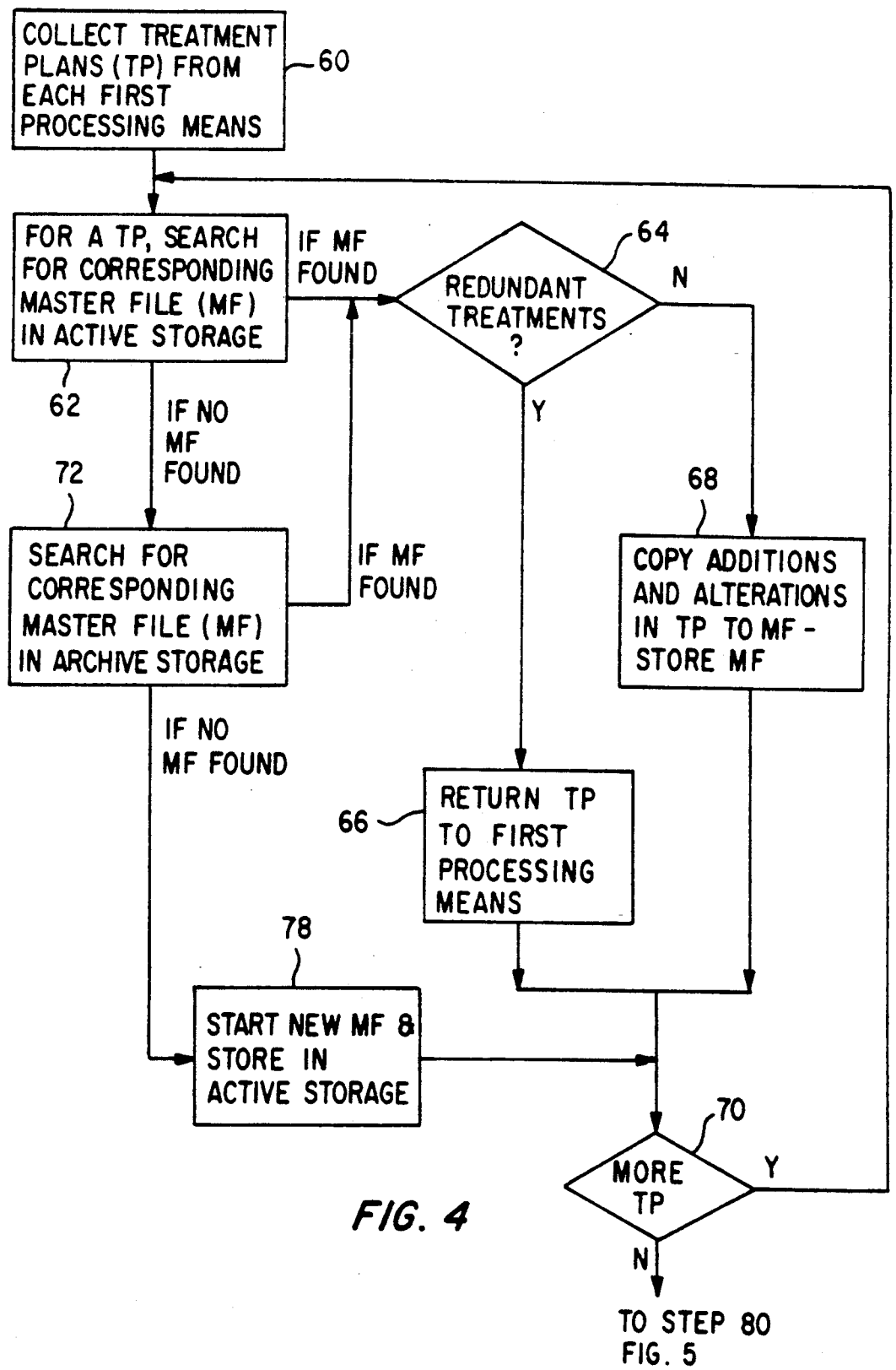
FIGS. 4 to 7 illustrate the processing of treatment plans and treatment records in accordance with a preferred embodiment of the present invention.

Once the treatment plan is received, the provider reviews the plan and determines if prior treatment has been performed by him. Referring to FIG. 3, if there has been prior treatment, then the second processing means 14, in step 40, searches for and retrieves a treatment record for reference. If this is the first treatment for an illness or injury, then a new treatment record is generated in step 42 on the second processing means 14. In step 42, the second processing means 14 also preferably automatically includes as part of the treatment record, identifying information such as the name of the provider or his firm's name, the provider's identification number and address. Also included is a treatment record identification number associated with the treatment plan identification number, the patient's and the insured's name, address, phone number and social security number.

The provider then reviews the treatment plan, any available treatment record previously generated by the provider and any available test results (e.g., x-rays, lab tests) to determine if the diagnosis in the treatment plan is acceptable. The second processing means 14 can also include the diagnostic database previously described as well as any other diagnostic software package which can analyze the information in the treatment record and the treatment plan to assist the provider in this determination. If the provider disagrees with the diagnosis and the recommended treatment plan, the provider and the physician that generated the treatment plan confer. Any resulting changes are indicated in the treatment plan.

The provider, in step 44, selects the treatments to be performed on the current date by selecting associated CPT or DRG codes from the treatment plan. Also, if any pharmaceutical prescriptions are necessary, they are entered and the prescription given to the patient and processed in the same fashion as previously described in relation to the first processing means 12. In step 46, the provider's charge for performing the medical procedure or procedures is entered into the second processing means 14. If this price is guaranteed, then it should match the price listed in the database 10. If the price is not a guarantee, then it may or may not match the listed price. In step 48, the date on which the procedures were completed is entered. Once any procedures are completed, the treatment record may be stored in step 50 into a directory in the second processing means 14 along with all other unprocessed treatment records for eventual transfer to the third processing means 16.

Referring to FIGS. 4 to 7, the processing by the third processing means 16, of the treatment plans generated on the first processing means 12 and of the treatment records generated on the second processing means 14, is described. The third processing means 16, in step 60, periodically contacts each first processing means 12 via modem to collect each treatment plan that has been generated. As the treatment plans are collected, each treatment plan is processed as follows. In step 62, the active storage area in the third processing means 16 is examined to see if there is a master file with the same identification number as the treatment plan. The master files are files containing records of previous treatments related to this treatment plan. This search is performed to determine if related treatment plans or records have been previously produced. The active storage area in the third processing means 16 stores master files that are active or are transitional. An active master file has at least one treatment with a specified duration that extends beyond the current date. In a transitional master file, all treatments should have been performed within a predetermined amount of time before the current date, for example, two months before the current date.

If a corresponding master file is located in the active storage area, then in step 64, the collected treatment plan and the corresponding master file are evaluated to determine if the new treatment specified in the treatment plan is redundant, thereby reducing the potential for fraudulent claims. If the treatment is redundant, in step 66, the treatment plan is returned to the first processing means 12 with a notice of rejection indicating the redundancy. The patient is also notified. If the treatments are not redundant, in step 68, the additions and the alterations in the collected treatment plan are copied into the corresponding master file and the master file is stored. The next treatment plan is then retrieved in step 70.

If a master file is not found in the active storage area in step 62, then in step 72, the archive storage area is searched for a corresponding master file. The archive storage area contains archived master files having treatments that should have been performed before the above mentioned predetermined amount of time before the current date. If a corresponding master file is found in the archive storage area, then steps 64, 66 and 68 are performed as needed.

If a corresponding master file is not found in archive storage area in step 72, then a new master file is generated by the third processing means 16 in step 78. It is generated by copying the relevant information from the treatment plan into the master file. Additionally, the master file is stored in the active storage area and the collected treatment plan is discarded.

Figure 5:
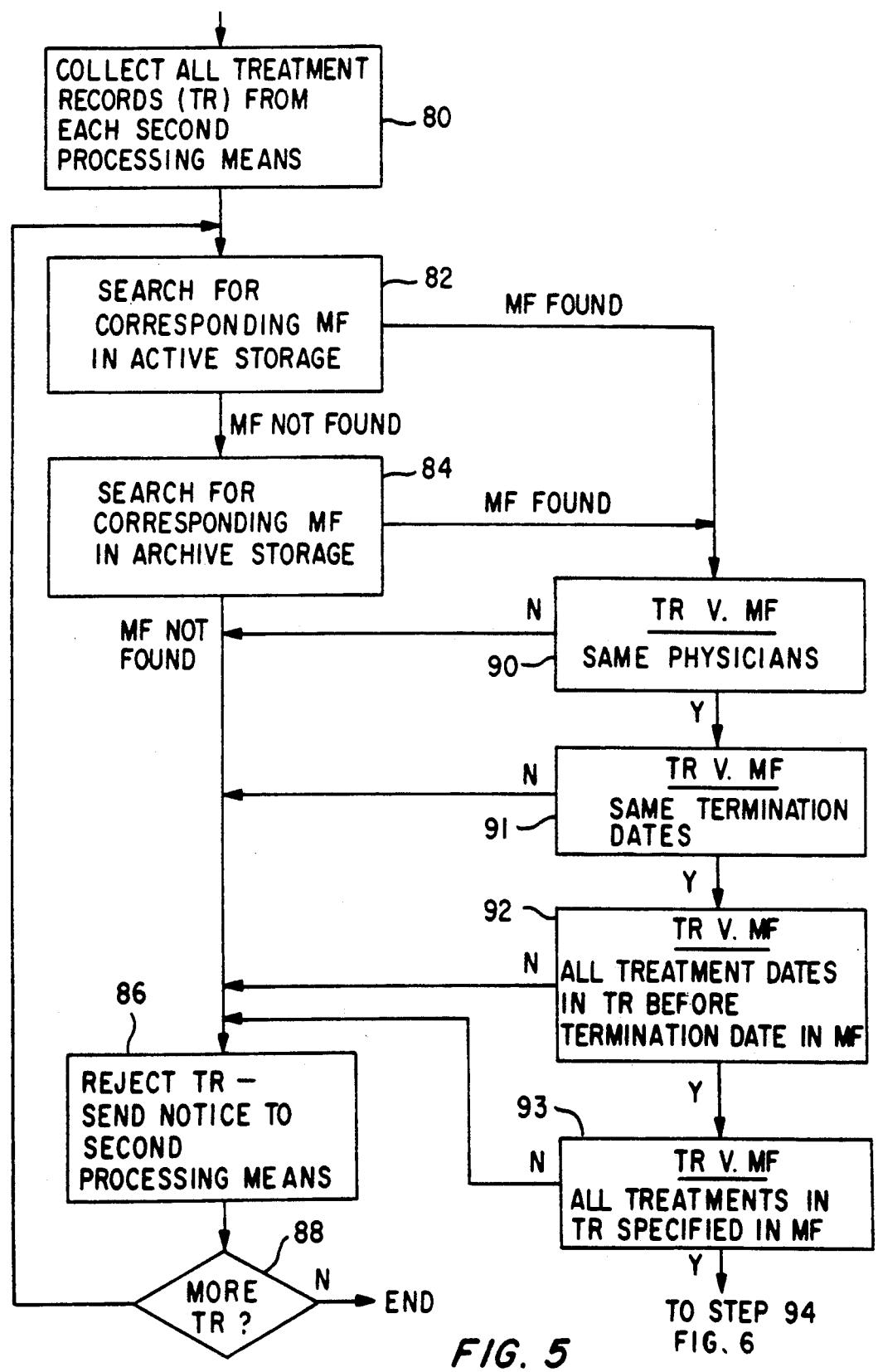

The above analysis continues until all collective treatment plans have been analyzed. Referring to FIG. 5, once all treatment plans have been analyzed, the third processing means 16 collects all of the generated treatment records from each second processing means 14, preferably via modem. Then, in step 82, the third processing means 16 examines the active storage area to determine if there is a corresponding master file. This is accomplished by examining the master file's identification number which is the same as the identification number in the related treatment plan and comparing it to the treatment record identification number.

If a corresponding master file is not found in the active storage area, then in step 84, the archived storage area is searched for a corresponding master file. If none is found, then in step 86, the treatment record is rejected and a notice of rejection is sent to the second processing means 14 indicating the reason for rejection. Then, in step 88, the next treatment record, if any, is sought for processing.

If a master file that corresponds to a collected treatment record is found in either the active or the archive storage areas, a series of security checks in steps 90 to 93 are performed by comparing the treatment record to the corresponding master file. In step 90, the comparison is made to determine if the same diagnosing physician is specified in the treatment record and in the master file. In step 91, the comparison is made to determine if the expiration dates in the treatment record and in the master file agree. In step 92, the comparison is made to determine whether the treatment date of the procedures in the treatment record are on or before the corresponding expiration date in the master file. In step 93, the treatment record is examined to verify that the treatments performed were specified by the master file. If the comparison in steps 90 or 91 do not match or if step 92 finds a treatment date after the termination date or if step 93 finds an unspecified procedure, all or part of the treatment plan is rejected by the third processing means 16 in step 86 and a notice of rejection is sent to the second processing means indicating the reason for the rejection.

Figure 6:
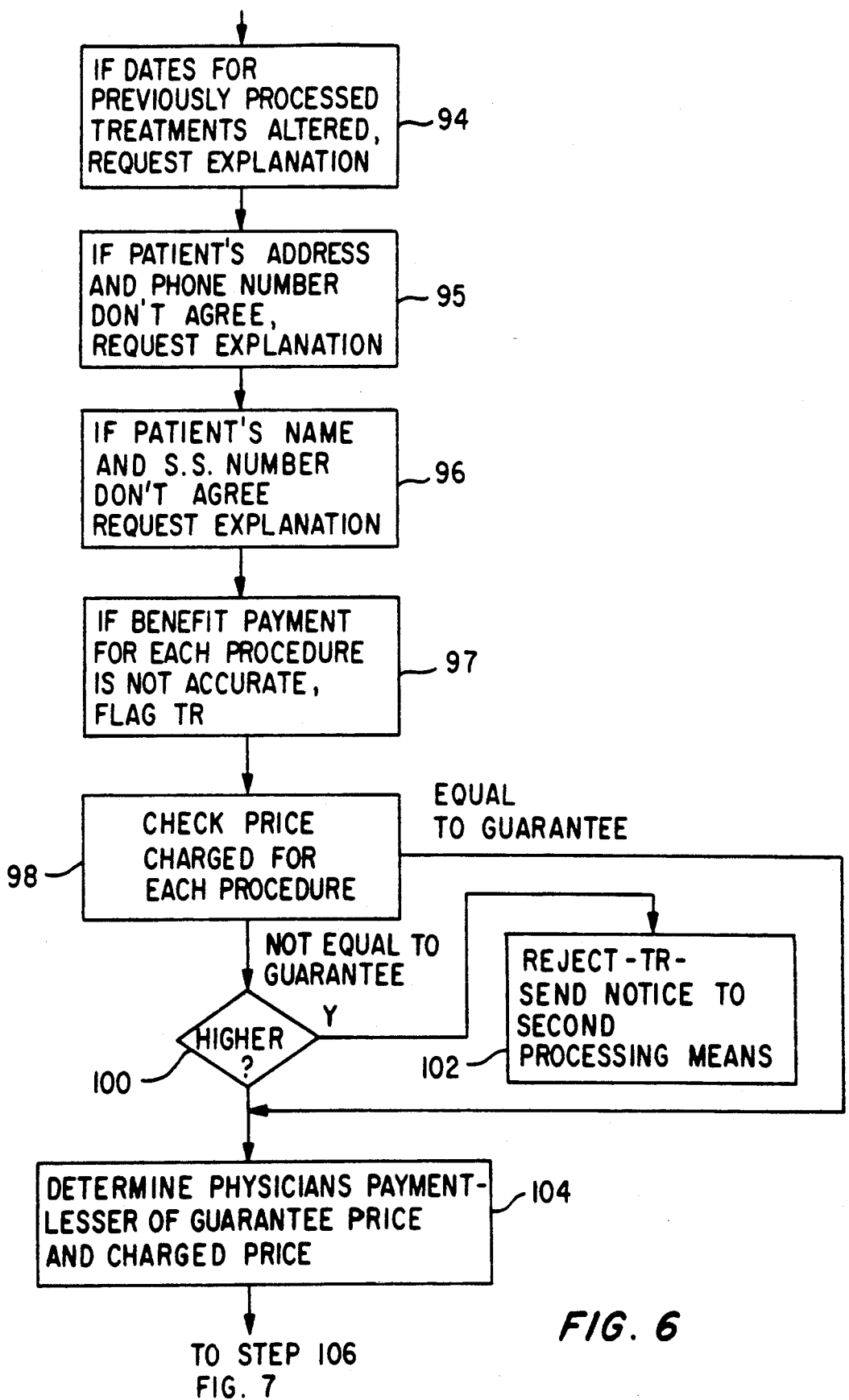

Referring to FIG. 6, if the security checks performed in the processing steps 90 to 93 are passed, then in step 94, the treatment dates in the master file associated with previously processed treatments are examined to see if alterations have been made. If they have, a request for explanation is sent to the second processing means 16. Next, in step 95, the master file and the treatment record are compared to see if the address and phone number information therein agree. In step 96, the master file and the treatment record are compared to see if the patient name and social security numbers therein agree. If, in steps 95 and 96, there is a disagreement, then a request for verification is sent to the second processing means 16.

The third processing means 16, in step 97, checks the database 10 to determine if the benefit payment for each procedure, as specified in the master file, is accurate. If a discrepancy is found, the treatment record is flagged so that an investigation into the reasons for the discrepancy can be started. Processing, however, continues regardless of whether a discrepancy is found.

In step 98, the third processing means 16 checks the amounts charged for each procedure to determine if they are in agreement with the guaranteed prices in the database 10. If they are not, in step 100, the third processing means 16 determines whether the amount charged is higher than the guaranteed price. If the amount charged is higher, then in step 102, all or part of the treatment record is rejected and a notice of rejection is sent to the second processing means 14. If the amount charged is lower than the guaranteed price, however, a request for explanation is sent to the second processing means 14, in step 104, and the lower amount charged is utilized to determine the amount due to the second processing means. In this case, the physician will receive the lesser of the lower amount charged and the benefit payable.

If, in step 98, the amount charged is in agreement with the guaranteed price, that amount is utilized in step 104 to determine the amount due to the provider. In this case, therefore, the provider will receive the lesser of the guaranteed price in the database 10 and the benefit payable.

Figure 7:
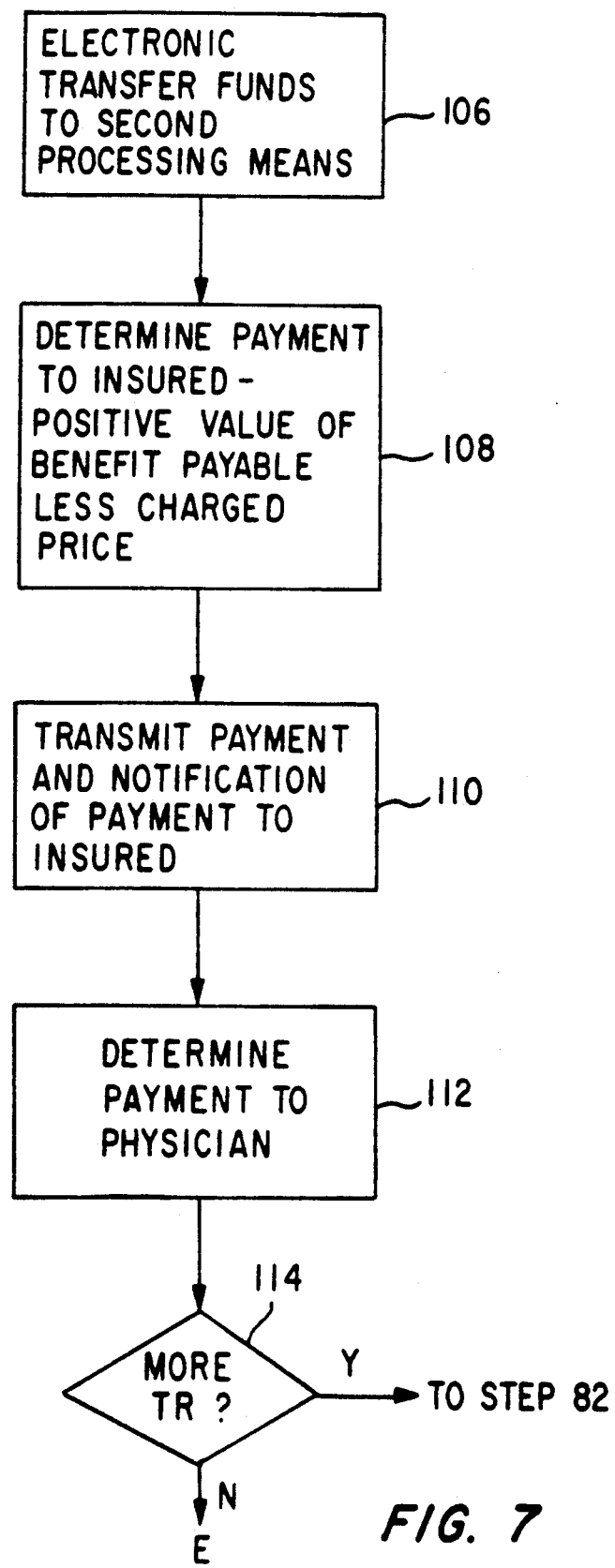

Referring to FIG. 7, in step 106, the amount due to the physician is preferably electronically transferred to the second processing means 14. The third processing means 16, in step 108, determines the amount due to the insured. This amount is the positive difference between the benefits payable for the procedures and the amounts charged. In step 110, a notification of payment to providers is issued to the insured along with a check for the amount due. If the amounts charged exceed the benefits payable, then the insured will be liable to the provider for this amount. In step 112, the master file is processed to determine the amount due the examining physician for procedures performed. In step 114, the next treatment record, if any, is retrieved and is processed starting at step 82.

The third processing means 16, in addition to the processing illustrated in FIGS. 4 to 7, also performs background processing. For example, the diagnostic database previously mentioned can also be generated by extracting relevant information from treatment plans and treatment records. As another example, the termination dates associated with treatment plans can be modified by the examining physician, when it is necessary to extend treatments. Such modifications are performed on a background basis. In addition, statistical evaluations could be performed on the diagnoses of the examining physicians to determine the reliability and completeness of the diagnoses. Similar analysis can be performed on all information received by the third processing means 16.

The steps illustrated in FIGS. 6 and 7 are based on the preferred embodiment wherein the price listed in the database 10 is a guaranteed price. If the listed price is merely a current price, the procedure can be modified so that the physician would receive the lesser of the benefit payable and the charge price. In this case, the insured would receive the positive value of the benefit payable less the charged price.

The system of the present invention also has special advantages for pharmaceutical prescriptions. As previously noted, prescriptions preferably become part of the treatment plan generated by the examining physician. In accordance with the preferred embodiment, the first processing means 12 would also generate a separate file containing the prescription information. Additionally, hard copies of the prescription can be produced automatically and signed by the examining physician if so desired. In the preferred embodiment, the database 10 would include price and source information on pharmaceutical prescriptions. This information would be appended to the treatment plan to assist the patient in selecting the pharmacy at which the prescription will be purchased. If the size of the database 10 is limited, then a limited number of drugs, preferably those most frequently prescribed as well as a limited number of suppliers, preferably those most conveniently located or exceptionally low priced, are included in the database 10. If information on a prescribed drug is not in the database 10, then the patient can obtain such information from a hard copy listing of sources and prices which can, for example, be maintained at the examining physician's office. The information can also be obtained directly from the first processing means 12.

The prescription information can be transmitted by the first processing means 12 directly to the second processing means 14 at the pharmacy. Alternatively, the patient can provide the selected pharmacist with the prescription on magnetic medium or on the hard copy. It is preferred that the second processing means 14 in the pharmacy contain a database that has background information concerning each prescription, such as warnings. When the prescription is filled and a label is printed out for the prescription, the database is accessed so that the warning information can be printed out on the label or on a separate listing. The information can also be provided in a database in the first processing means 12 and can be appended to the treatment plan. The processing by the second processing means 14 at a pharmacy is similar to that before described. The processing by the third processing means 16 of the claims by the pharmacy is accomplished in the same way as described in relation to FIGS. 4 to 7.

Referring back to FIG. 1, such a system can be implemented in a variety of ways. In a preferred embodiment, a distributed processing system is used to prevent fraud. The first processing means 12 is provided in the offices of each physician performing diagnostic examinations and the second processing means 14 is provided in the offices of each provider performing medical treatment procedures. The interconnections between the database 10 and each processing means in each office are provided as illustrated in FIG. 1 via modem. The database 10 is preferably provided in each first processing means 12 but can also be provided in the third processing means 16 for access by each first processing means 12. In an alternative embodiment, the database 10, the first processing means 12, the second processing means 14 and the third processing means 16 can be part of a central processor. In this case, data entry means are provided in the office of each physician who performs diagnostic examinations to provide access to the first processing means 12 in the central processor. Also, data entry means are provided in the office of each provider who performs medical procedures to permit access to the second processing means 14.

What is claimed is:

1. An automated system for processing health benefit claims by an insured, comprising:

a database that, for each of a plurality of procedures, specifies a benefit payable in the event the procedure is prescribed and performed, a list of medical treatment providers available for performing the procedure and each provider's charge for performing the procedure;

first processing means for generating a treatment plan that specifies the identity of the insured and one or more procedures to be performed on the insured and for accessing the database to append to the treatment plan the benefit payable, the list of medical treatment providers and each provider's charge, for each procedure to be performed;

second processing means for generating a treatment record that specifies, from/the procedures to be performed pursuant to the treatment plan, one or more procedures actually performed on the insured and the actual charge for performing each of the procedures; and third processing means for processing the treatment plan and the treatment record to determine an amount payable to the insured equalling the amount by which the benefit payable for the procedures actually performed less the actual charges for performing the procedures exceeds zero.

2. The system as claimed in claim 1, wherein the second processing means specifies the identity of the medical treatment provider actually performing the procedures in the treatment record and the third processing means also determines an amount payable to the medical treatment provider equalling the lesser of the actual charges and the benefit payable for the procedures actually performed.

3. The system as claimed in claim 2, wherein the third processing means, prior to determining amounts payable to the insured and to the medical treatment provider, performs security checks by comparing the treatment plan to the treatment record and terminates processing without payment to the insured or to the medical treatment provider if the comparison yields a mismatch.

4. The system as claimed in claim 3, wherein the procedures actually performed, as specified by the treatment record are checked against the procedures to be performed, as specified by the treatment plan, to ensure that the proper procedures were actually performed.

5. The system as claimed in claim 4, wherein identifying information is included in the treatment plan by the first processing means and in the treatment second by the record processing means and the third processing means compares the identifying information.

6. The system as claimed in claim 1, wherein the medical treatment provider's charge in the database is updated by the third processing means based of the medical treatment provider's latest actual charges for performing the procedure.

7. The system as in claim 1, wherein the list of medical treatment providers available for performing the procedure designated in the database is further subdivided by geographic areas.

8. The system as claimed in claim 1, wherein background information concerning each medical treatment provider is included in the database.

9. The system as claimed in claim 8, wherein the background information includes experience for each procedure, medical specialties, board certifications, years in practice, medical degrees, class rank, residency location, malpractice suits lost and settled, hospital affiliations, university affiliations and any credit cards by which payment can be made.

10. The system as claimed in claim 1, wherein the treatment plan includes any pharmaceutical prescriptions.

11. The system as claimed in claim 10, wherein the database includes background information concerning the pharmaceutical prescription which the first processing means includes in the treatment plan.

12. The system as claimed in claim 1, wherein the information in the database is organized under individual procedures.

13. The system as claimed in claim 1, wherein the information in the database is organized under a group of procedures to be performed according to an episode of illness.

14. The system as claimed in claim 1, wherein each medical treatment provider sought by the insured has access to the second processing means for generating a treatment record and the third processing means compares each treatment record to the treatment plan to determine amounts payable.

15. The system as claimed in claim 1, wherein physicians generate treatment plans for insureds on the first processing means, medical treatment providers generate treatment records for insureds on the second processing means and the third processing means compares each treatment plan to the appropriate treatment records to determine settlement amounts payable.

16. The system as claimed in claim 15, wherein the database, the first processing means, the second processing means and the third processing means are provided in a central processor.

17. The system as claimed in claim 15, wherein the database and the first processing means is located in each physicians' office that generates treatment plans and the second processing means is located in each medical treatment providers' office that generates treatment records.

* * * * *